US006195409B1

(12) United States Patent
Chang et al.

(10) Patent No.: US 6,195,409 B1
(45) Date of Patent: Feb. 27, 2001

(54) AUTOMATIC SCAN PRESCRIPTION FOR TOMOGRAPHIC IMAGING

(75) Inventors: Linda Chang; Thomas M. Ernst, both of Redondo Beach; Laurent Itti, Pasadena, all of CA (US)

(73) Assignee: Harbor-UCLA Research and Education Institute, Torrance, CA (US)

( * ) Notice: Subject to any disclaimer, the term of this patent is extended or adjusted under 35 U.S.C. 154(b) by 0 days.

(21) Appl. No.: 09/272,436

(22) Filed: Mar. 19, 1999

Related U.S. Application Data

(60) Provisional application No. 60/086,401, filed on May 22, 1998.

(51) Int. Cl.[7] .................................................. A61B 6/03
(52) U.S. Cl. ........................... 378/20; 378/4; 378/8; 378/901
(58) Field of Search .............................. 378/4, 8, 20, 901

(56) References Cited

U.S. PATENT DOCUMENTS

| | | | |
|---|---|---|---|
| 4,884,566 | 12/1989 | Mountz et al. | 606/130 |
| 5,218,623 | 6/1993 | Toki et al. | 378/4 |
| 5,454,019 | 9/1995 | Migita et al. | 378/15 |
| 5,583,903 | 12/1996 | Saito et al. | 378/19 |
| 5,590,164 | 12/1996 | Kawai et al. | 378/4 |
| 5,668,846 | 9/1997 | Fox et al. | 378/4 |
| 5,672,877 | 9/1997 | Liebig et al. | 250/363.04 |
| 5,951,475 | * 9/1999 | Gueziec et al. | 600/425 |
| 6,023,495 | * 2/2000 | Adler et al. | 378/4 |
| 6,028,907 | * 2/2000 | Adler et al. | 378/4 |

* cited by examiner

*Primary Examiner*—David V. Bruce
*Assistant Examiner*—Allen C. Ho
(74) *Attorney, Agent, or Firm*—Fulwider Patton Lee & Utecht, LLP

(57) ABSTRACT

The system and method for automatic scan prescription involves initially performing at least one localizer scan for the object being imaged. The localizer images are analyzed to extract important structural information about the object of interest, and of subobjects of interest, yielding an abstract, schematic description of the object of interest. Optimal spatial locations and scanning parameters are then determined for subsequent scans from the information about the object, possible subobjects, and their relationship to a template. The locations for a particular scan included in a set of protocols selected by the operator are then communicated to the scanner in order to automatically drive the scanner. In a presently preferred embodiment, all of the analysis, matching, and scan prescription operations are preferably carried out by a microprocessor based microcomputer. Subsequent detailed and radiologically relevant scans can then be performed using optimal scanning parameters for the patient.

29 Claims, 2 Drawing Sheets

AUTOMATIC SCAN PRESCRIPTION FOR TOMOGRAPHIC IMAGING

RELATED APPLICATIONS

This is based upon the provisional application Serial No. 60/086,401 filed May 22, 1998.

BACKGROUND OF THE INVENTION

1. Field of the Invention

This invention relates generally to medical imaging, and more particularly concerns a method for automatic scan prescription for tomographic imaging, such as magnetic resonance imaging (MRI), computer tomography (CT), and other tomographic imaging techniques. More specifically, the invention relates to methods to automatically determine scan orientations and locations for tomographic imaging scans.

2. Description of Related Art

In computerized tomography (CT), an image of a section or slice of a region of interest of a patient is typically obtained from a large number of narrow X-ray beam projections, at multiple angles through the slice, for providing multiplanar imaging of the patient. Modern CT scanners commonly provide a detector array mounted opposite the X-ray source, or a ring of detectors completely surrounding the region of interest of the patient, that sequentially detect the X-ray source as it is rotated around the patient. From the many individual measurements from the detectors, from either a single slice, a series of slices, or a helical scan, a computer is commonly used to fill in image data for a matrix of pixels with digital values representing the X-ray intensity measured during the scans.

While the human eye can only differentiate a limited number of shades of gray, computerized digital image data with much finer gradations can be utilized for identification and recognition of structures. One known X-ray computed tomography system is capable of specifying a slice plane corresponding to a desired tomographic image from a data base of helical or multiple scans of a subject. A scanogram of the subject is displayed, on which a cursor is controlled to identify the desired slice planes corresponding to the desired tomographic images to be reconstructed. The desired tomographic images are reconstructed for the desired slice planes indicated by the cursor by using an appropriate portion of the projection data, corresponding to the desired slice planes indicated by the cursor.

Another computed tomography system is known that includes an image reconstruction data generator for generating image reconstruction data for a desired slice plane of an object in accordance with projection data obtained at a plurality of rotation positions of a radiation source. The system also includes an image reconstructor for obtaining tomographic image data of the object for the desired slice plane, according to the image reconstruction data.

While CT can-be more advantageous for scanning bone structures than magnetic resonance imaging (MRI), MRI scanning is advantageous for imaging soft tissue structures, and can be used for multiplanar imaging of a patient. One such MRI imaging system is known, for example, for determining an MRI image plane, such as for imaging the head of a human being, in which the location of the plane of imaging, and its orientation are determined by computer analysis of the distance between manually selected points of the image, and the ratios of the distances between them.

Despite numerous advances in image processing of scanned images, tomographic scanning of patients for medical purposes is still generally performed according to manual prescriptions by specially trained medical technologists. In conventional tomographic imaging, prescription of scanning orientations, locations and angles requires a considerable amount of detailed input and control by the medical technologist. A typical scanning session begins with the acquisition of a "localizer" or "pilot" scan which provides an overview of major anatomical features, such as size and position, of a patient's body or body part to be scanned. Following the localizer scan, several additional scans are usually performed to gain more detailed information about the portion of the patient of interest. For each additional scan, the medical technologist uses the localizer scan or previous scans to manually define the boundaries and the orientation of the spatial volume to be scanned, such that it fully includes the region of interest.

Such conventional procedures for manually prescribing scan locations are relatively time consuming. As a result, human operators of tomographic imaging devices spend a considerable percentage of their time on this task, and are commonly unable to finish the manual prescription for a next scan before a current scan is finished, resulting in inefficient use of valuable scan time.

Currently, a scan technologist piloting the scanner equipment attempts to manually define scanning parameters that are appropriate for each individual patient. However, manual scan prescription by human operators is often crude, as the operators usually are not able to fully explore all degrees of freedom that need to be optimized in order to obtain the best possible scan. For example, many scanning parameters such as rotations of the tomographic imaging plane are kept at their default value. One of the consequences of this limited use of the available scanning parameters is an inaccurate, non-standardized prescription, yielding scan orientations that vary from one individual to another. With medical scans, such a variability in the scans makes interpretation of the scanned images by radiologists more difficult, and may ultimately lead to reduced quality of radiologic readings.

Another consequence of the variability in the scan orientations is poor reproducibility for repeat scans, i.e., very different images are usually obtained when the same subject is scanned in different sessions, for example for follow-up of medical conditions, making direct comparison of scans from different sessions difficult.

It can thus be readily appreciated that there is a need for a method and system for automatic prescription of tomographic scans, according to standardized protocols, that minimizes the involvement of a human operator, and that permits reproducible multiple scanning of the same object or organ at different points in time. Such a method would be advantageous for providing accurate and reproducible prescriptions for studies that depend on one or more previous prescriptions. It would also be desirable to provide a method for automatic definition of specific regions of interest within a larger object or organ of interest in the tomographic imaging device for use with scanning methods to obtain information from the specific regions of interest, such as for localized magnetic resonance spectroscopy, for example, to obtain chemical information from within a well defined region of interest.

The present invention meets these needs.

SUMMARY OF THE INVENTION

Briefly, and in general terms, the present invention provides for a method for automatically prescribing scans for tomographic imaging, and in particular for magnetic resonance imaging or computed tomography. The method of the invention for providing an automatic scan prescription allows faster, more reliable, more reproducible and more complicated scan prescriptions than are achievable manually by human operators. The system and method of the invention can be utilized in conjunction with a scanner, using a standard computer network apparatus, to communicate and automatically pilot the scanner. The system and method of the invention provide for fully automatic scan prescription and operation of a scanner, so that the only manual steps necessary for an operator to carry out a fall tomographic study with multiple prescribed scans are to place a patient in a scanner and to select a clinical imaging protocol from a list of available choices.

The invention accordingly provides for a system and method for determining the orientation and location of standard tomographic scanning planes for automated scan prescription. Initially one or more initial localizer scans are performed. In one presently preferred embodiment, the one or more localizer scans may be used to determine a minimal bounding box for the object of interest to be imaged. The initial rapid localizer scan or scans can be, for example, a sagittal scan to determine the inferior/superior (I/S) range, i.e., a top and bottom range, and/or to determine the anterior/posterior (A/P) range of a bounding box for the object of interest. Alternatively, the initial rapid localizer scan can be an axial scan to determine the anterior/posterior (A/P) range, and/or the left/right (LR) range of the bounding box for the object of interest. As a further alternative, the initial rapid localizer scan can be a coronal scan to determine the left/right (LR) range or inferior/superior (I/S) range of the bounding box for the object of interest. This bounding box is defined as a rectangular boundary in terms of coordinates, and can then be utilized to prescribe further regular axial, sagittal or coronal scans. If a more special scan is necessary, another set of images can be obtained showing more detail.

The localizer images also may be analyzed to extract important structural information about the object of interest, such as the size, location, and orientation of the object or organ of interest, and of subobjects of interest, yielding an abstract, schematic description of the object of interest. For brain scans, such features may include, but are not limited to, the outer surface of the brain, the center locations of the eyes, and the locations of the brain commissures.

Significantly, the abstract, schematic description of (the "model") of the object of interest is then matched with a reference template of the abstract, schematic description of the object of interest that additionally contains information about the location of standard, optimal scanning planes, orientations and boundaries. Optimal spatial locations and scanning parameters can then be determined for subsequent scans from the information about the object, possible subobjects, and their relationship to the template. The locations for a particular scan included in a set of protocols selected by the operator are then communicated to the scanner in order to automatically drive the scanner. In a presently preferred embodiment, all of the analysis, matching, and scan prescription operations are preferably carried out by a microprocessor based microcomputer. Subsequent detailed and radiologically relevant scans can then be performed using optimal scanning parameters for that patient.

These and other aspects and advantages of the invention will become apparent from the following detailed description and the accompanying drawings, which illustrate by way of example the features of the invention.

DETAILED DESCRIPTION OF THE PREFERRED EMBODIMENTS

Scan locations are usually prescribed by technologists, who manually define the boundaries and the orientation of the spatial volume to be scanned, such that it fully includes the organ of radiological interest. However, manual prescription of scan operations for tomographic imaging devices is time consuming, inefficient, and non-standardized, yielding scan orientations that vary from one individual to another, and that vary for a given individual from one scan to the next, making interpretation of the scanned images difficult.

Figure 1:
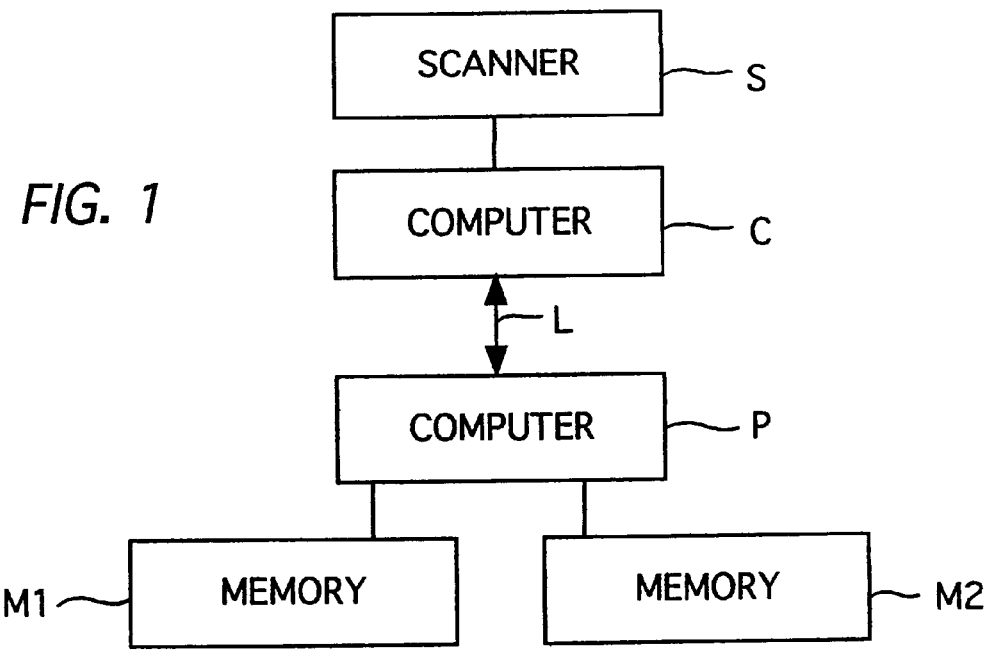
FIG. 1 is a schematic diagram of the system for determining the orientation and location of tomographic scanning planes for automated scan prescription, according to the principles of the invention.

Accordingly, as is illustrated in the drawings, and with reference to the attached Appendix containing source code for software utilized in the invention, the invention provides for a method for determining the orientation and location of tomographic scanning planes for automated scan prescription. Referring to FIG. 1, the scanner consists of a tomographic imaging device, or scanner S, such as is generally available from General Electric, Siemens, Philips, and other manufacturers. The scanner is controlled by a computer, C. The device for automatic prescription consists of a computer P which is able to communicate with the scan computer C via a computer link L. Memory M1 of computer P holds one or more templates for scan prescriptions. Memory M2 of computer P holds a list of imaging protocols which may be selected by a human operator. For purposes of illustration, computer P and associated memory M1, M2, is shown to be physically different from computer C. However, computer P and associated memory maybe physically identical to computer C and associated memory, in which case computer C and computer P represent different processes orprograms within the same computer, and link L represents interprocess communication.

Figure 2:
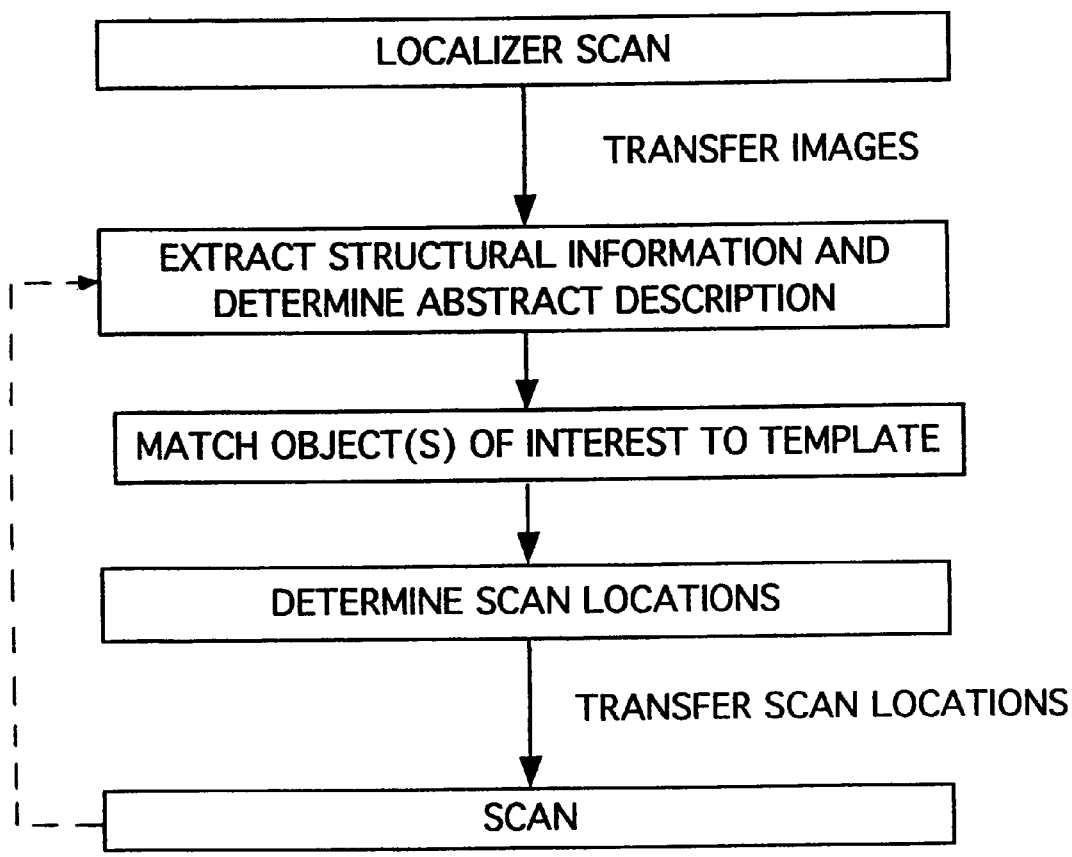
FIG. 2 is a flow chart of the computer software algorithms utilized in carrying out the invention.

With reference to FIG. 2, showing a flow chart of the method of the invention, in step 1, an initial localizer scan of the object of interest is performed on the scanner S and computer C. The resulting localizer images are transferred to computer P via link L. In step 2, the localizer images are analyzed in computer P to extract important structural information, such as size, location, and orientation, about the object and possible subobjects under consideration, yielding an abstract, schematic description (a "moderl") of the object of interest. In step 3, a computer algorithm matches the abstract description (i.e. the model) of the object and subobjects of interest to the model of a template. In step 4, the information about the object, possible subobjects, and their relationship to the template is used to determine scan locations. In step 5, the scan locations are transferred back to the scanner to drive the scanner. The images from new scans may be used as additional localizer images, as indicated by an arrow pointing from step 5 to step 2 in FIG. 2.

The "model" is an abstract, schematic description of the object of interest. The model consists of geometric information in the form of "vertices" and possibly structural information in the form of "links" between the vertices and in the form of the "rigidity" of the links. The model thus corresponds to geometric and physical attributes of the object of interest. Each vertex of the model corresponds to a two or three dimensional set of coordinates identifying such features as the tip of the nose, an eye, brain commissures, and other similar reference points that correlate with anatomical structures. The vertices of the current patient are to be matched to be as close as possible to the corresponding vertices in the template. The links between vertices are defined in the form of vectors of distance or line segments, and a spring force identifying some physical relation between the points. The computer determines the vertices of the sample image according to model matching algorithms, further described below.

Figure 3:
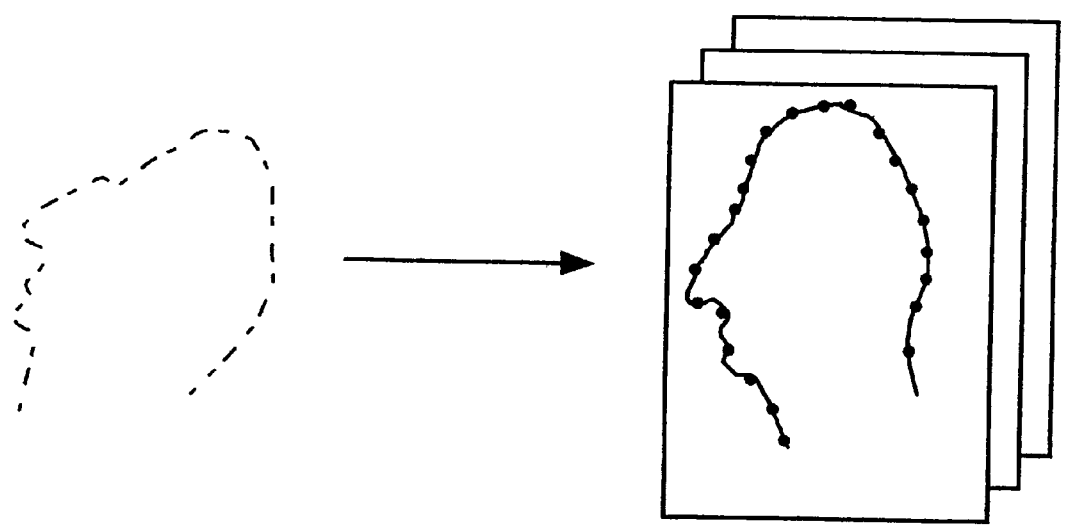
FIG. 3 is a schematic diagram of an initial level of matching of a skin contour of an image to a generic head shape.

Several models or templates are used for the different steps or stages of the automatic scanning sequence. The initial levels of modeling are very gross, but very robust, and can be as simple as a bounding box or a surface contour of a magnetic resonance (MR) image, for example to a generic head shape, as illustrated in FIG. 3. This step may be used to determine head size and orientation in a fully automatic manner. Other models can be defined for the brain, brain structures, cranial structures, other organ structures, and the like. The models may be hierarchical; for example, a head model may include a boundary box, a skin surface model, a brain model, and an internal brain structure model. In a hierarchical system, an expert system checks various matching rules, such as checking matches of the vertices for the eyes, the skin contour, or brain commissures. In this manner, the model will predict that eyes will be in a certain location of an image, and evaluates whether the location of the image has image features similar to those for eyes, or for the skin contour, for example, by matching such features as brightness or intensity of the pixels at the location, and the shape of one or more groups of pixels at the location.

This allows for automatic quality control and makes the automatic scanning sequence robust.

Model matching uses geometric transformations (rigid or non-rigid) such that the model is moved, rotated, stretched, smeared or whatever other geometric transformation may be necessary to obtain a good fit between the generic model or template, and the particular image data. The steps in the transformation process are iterative, occurring for all of the possible transformations in tiny steps in loops. The rigidity of a link between two vertices of the model defines the strength of the relationship between the corresponding vertices. The rigidity of a link between two vertices generates a force, which depends upon the distance between the vertices. In one preferred embodiment of the invention, the force is mathematically similar to a spring force, in that the force of the link between vertices is increasing with the distance between the vertices. An energy balance of all of the spring forces and the changes in the distances between the vertices is determined for each step of the transformation process in conforming the model to the image, so that competition between the spring forces of the vertices counteracts unrealistic distortions of the models, and the looping of the transformation process continues as long as the forces do not completely balance.

The invention exploits several strategies and uses an expert system applying a set of rules prescribed by the operator to determine which strategy to apply. For example, an initial head orientation may first be estimated by fitting a bounding box, and then a skin contour model, and then a brain model. Next, the system could check whether the eyes are close to the location predicted by the model. If after proceeding through the possible matches, the match is determined to have failed, such as by achieving 7 positive matches and 3 negative matches out of 10, for example, the system can step through the various geometric transformations again and check the hierarchical matching, until a model transformation is found that satisfies enough of the quality control tests.

Once a sample is matched with a template, the various scanning planes of the sample image are determined from the known planes of the template, allowing the reliable, precise and accurate prescription of new scans for regions of interest in an automatic fashion.

A typical scan acquisition process can have the following sequence, for example. 1) The system scans the subject and acquires a sagittal, fall field image; 2) the image is matched to a bounding box model; 3) the image is matched to the skin surface, using a starting position for the skin model that is inferred from the bounding box; 4) selected internal structures are matched to a model of internal structures, using the skin contour model matching as a basis to infer the starting position of the internal structure model; 5) the position and location of the matched models are used to determine standard scanning planes, such as the orbital metal plane, the anterior commissures-posterior commissure line, and the scanning angles and boundaries for a prescribed scan for an region of interest.

For example, a fast spin echo (FSE) scan, an imaging sequence that is very rapid, was performed to study the brain of a subject, with scans being taken in the coronal, transverse and sagittal directions. The scans were utilized to create "water images" showing only pixels containing pure fluid, i.e. cerebrospinal fluid. From these images, an orbito-meatal plane (a standard reference line defined by the brain structures) and its rotation was identified, by co-registering the brain surface (from the images) with the reference brain with a known orbito-meatal line. Along the x-axis, the angle of orientation ($\gamma$) of the orbito-meatal plane of the current patient from the point of view of the scanner, i.e., the orientation of a scan along the orbito-meatal plane, was determined as the reference angle ($\rho$) plus the angle difference ($\alpha$) between the reference and the current patient from co-registration, as follows:

$$\gamma = \rho + \alpha$$

where the reference angle $\rho$ is the angle of the orbito-meatal plane in the reference images from the point of view of the scanner.

Planes may similarly be rotated about the y-axis or the z-axis if the head position is skewed, to adjust scans to match those known from the template. Also, by co-registering the image of the patient with a reference patient, spectroscopy voxels/pixels, such as for NMR spectroscopy, for example, can be prescribed in an automated fashion. It is also possible to use a gray/white segmentation to minimize or predetermine the grey/white content of voxel/pixel, i.e., to determine the chemical content of the gray/white matter. Similarly, scan planes can be placed for chemical shift imaging (CSI), a spectroscopy method, to scan multiple regions at one time.

Partial coverage of brain may also be obtained by coregistration. In certain situations, one may only want to scan certain subregions, such as the pituitary. In more complicated cases, the position may be obtained by complete segmentation to match a pituitary region to a template. It should be apparent that the principles of the invention can be applied to image processing of organs other than the brain.

For example, it is difficult to manually prescribe scan planes in the spinal cord, since it is bent; therefore, automatic prescription of the scan planes to follow the spinal cord would be an advantage. The scans used to extract information for automatic prescription are not limited to regular MRI sequences; more specialized scans, such as fat saturation scans, also may be used to extract anatomical information. Some pilot scans may be done using projection scans (full mass, i.e., of water in the brain), line scans, and the like, instead of fall three-dimensional scans. Echo planar imaging (EPI) is another extremely rapid scan technique, taking approximately 50 ms per scan, allowing 10–20 scans per second, that may also be suitable for use with the method of the invention.

It will be apparent from the foregoing that while particular forms of the invention have been illustrated and described, various modifications can be made of the invention. Accordingly, it is not t as by the appended claims.

What is claimed is:

1. A method for determining the orientation and location of standard tomographic scanning planes for automated scan prescription for a patient, the method comprising the steps of:
   a) performing at least one initial localizer scan of a patient to provide images for the object of interest to be imaged;
   b) analyzing the localizer scan images to extract important structural information about the object of interest to yield an abstract, schematic description of the object of interest;
   c) matching said abstract, schematic description of the object of interest with a reference template of the abstract, schematic description of the object of interest;
   d) determining optimal spatial locations and scanning parameters for subsequent scans based upon the relationship of the abstract, schematic description of the object of interest to the template;
   e) communicating locations for a desired scan to a scanner in order to automatically drive the scanner; and
   f) performing subsequent detailed scans to obtain detailed scan images based upon said optimal scanning locations and parameters for the patient.

2. The method of claim 1, further comprising the step of determining a minimal bounding box for the object of interest to be imaged from said at least one initial localizer scan.

3. The method of claim 1, wherein said at least one initial localizer scan comprises a sagittal scan.

4. The method of claim 2, wherein said at least one initial localizer scan comprises a sagittal scan, and further comprising the step of determining an inferior/superior range of said bounding box for the object of interest, based upon said sagittal scan.

5. The method of claim 2, wherein said at least one initial localizer scan comprises a sagittal scan, and further comprising the step of determining an anterior/posterior range of said bounding box for the object of interest, based upon said sagittal scan.

6. The method of claim 1, wherein said at least one initial localizer scan comprises an axial scan.

7. The method of claim 2, wherein said at least one initial localizer scan comprises an axial scan, and further comprising the step of determining the anterior/posterior range of the bounding box for the object of interest, based upon said axial scan.

8. The method of claim 2, wherein said at least one initial localizer scan comprises an axial scan, and further comprising the step of determining the left/right range of the bounding box for the object of interest, based upon said axial scan.

9. The method of claim 1, wherein said at least one initial localizer scan comprises a coronal scan.

10. The method of claim 2, wherein said at least one initial localizer scan comprises a coronal scan, and further comprising the step of determining a left/right range of the bounding box for the object of interest, based upon said coronal scan.

11. The method of claim 2, wherein said at least one initial localizer scan comprises a coronal scan, and further comprising the step of determining an inferior/superior range of the bounding box for the object of interest, based upon said coronal scan.

12. The method of claim 2, wherein said bounding box is defined as a rectangular boundary in terms of coordinates, and further comprising the step of prescribing at least one further scan selected from the group consisting of a regular axial scan, a regular sagittal scan, and a coronal scan.

13. The method of claim 1, wherein said step of analyzing the localizer images to extract important structural information comprises determining size, location, and orientation of the object or organ of interest.

14. The method of claim 1, wherein said step of analyzing the localizer images to extract important structural information comprises determining size, location, and orientation of a sub-object of interest.

15. The method of claim 1, wherein said reference template contains information about the location of standard, optimal scanning planes, orientations and boundaries.

16. The method of claim 1, further comprising repeating steps b)–f), utilizing the detailed scan images of step f) as the localizer scan images of step b).

17. A system for determining the orientation and location of standard tomographic scanning planes for automated scan prescription, comprising:
   means for performing at least one initial localizer scan for the object of interest to be imaged;
   means for analyzing the localizer images to extract important structural information about the object of interest to yield an abstract, schematic description of the object of interest;
   means for matching the abstract, schematic description of (the "model") of the object of interest with a reference template of the abstract, schematic description of the object of interest;
   means for determining optimal spatial locations and scanning parameters for subsequent scans from the information about the object, possible sub-objects, and their relationship to the template;
   means for communicating the locations for a particular scan included in a set of protocols selected by the operator to the scanner in order to automatically drive the scanner; and
   means for performing subsequent detailed and radiologically relevant scans using optimal scanning parameters for that patient.

18. The system of claim 17, further comprising means for determining a minimal bounding box for the object of interest from said at least one initial localizer scan.

19. The system of claim 18, wherein said at least one initial localizer scan comprises a sagittal scan, and further comprising means for determining an inferior/superior range of said bounding box for the object of interest, based upon said sagittal scan.

20. The system of claim 18, wherein said at least one initial localizer scan comprises a sagittal scan, and further comprising means for determining an anterior/posterior range of said bounding box for the object of interest, based upon said sagittal scan.

21. The system of claim 18, wherein said at least one initial localizer scan comprises an axial scan, and further comprising means for determining the anterior/posterior range of the bounding box for the object of interest, based upon said axial scan.

22. The system of claim 18, wherein said at least one initial localizer scan comprises an axial scan, and further comprising means for determining the left/right range of the bounding box for the object of interest, based upon said axial scan.

23. The system of claim 18, wherein said at least one initial localizer scan comprises a coronal scan, and further comprising means for determining the left/right (LR) range of the bounding box for the object of interest.

24. The system of claim 18, wherein said at least one initial localizer scan comprises a coronal scan, and further comprising means for determining the inferior/superior (I/S) range of the bounding box for the object of interest.

25. The system of claim 18, wherein said bounding box is defined as a rectangular boundary in terms of coordinates, and further comprising means for prescribing at least one further scan selected from the group consisting of a regular axial scan, a regular sagittal scan, and a coronal scan.

26. The system of claim 18, wherein said means for analyzing the localizer images to extract important structural information comprises means for determining size, location, and orientation of the object or organ of interest.

27. The system of claim 18, wherein said means for analyzing the localizer images to extract important structural information comprises means for determining size, location, and orientation of a sub-object of interest.

28. The system of claim 18, wherein said reference template contains information about the location of standard, optimal scanning planes, orientations and boundaries.

29. The system of claim 18, wherein said means for analyzing the localizer images, said means for matching, and said means for determining optimal spatial locations and scanning parameters comprise a microprocessor based microcomputer.

* * * * *